(12) United States Patent
Baloa Welzien et al.

(10) Patent No.: US 9,669,173 B2
(45) Date of Patent: Jun. 6, 2017

(54) CONTINUOUS POSITIVE AIRWAY PRESSURE THERAPY AUTO-TITRATION

(71) Applicant: Breathe Technologies, Inc., Irvine, CA (US)

(72) Inventors: Leonardo Alberto Baloa Welzien, Lake Forest, CA (US); Masoud Vahidi, Laguna Hills, CA (US); Samir S. Ahmad, San Diego, CA (US)

(73) Assignee: Breathe Technologies, Inc., Irvine, CA (US)

( * ) Notice: Subject to any disclaimer, the term of this patent is extended or adjusted under 35 U.S.C. 154(b) by 732 days.

(21) Appl. No.: 14/104,842

(22) Filed: Dec. 12, 2013

(65) Prior Publication Data

US 2015/0165143 A1     Jun. 18, 2015

(51) Int. Cl.
| | |
|---|---|
| *A61M 16/00* | (2006.01) |
| *A61B 5/00* | (2006.01) |
| *A61B 5/1455* | (2006.01) |
| *A61M 16/06* | (2006.01) |
| *A61M 16/20* | (2006.01) |

(52) U.S. Cl.
CPC ..... *A61M 16/0069* (2014.02); *A61B 5/14551* (2013.01); *A61B 5/4818* (2013.01); *A61B 5/4836* (2013.01); *A61M 16/0051* (2013.01); *A61M 16/06* (2013.01); *A61M 16/208* (2013.01); *A61M 2016/0027* (2013.01); *A61M 2205/3344* (2013.01); *A61M 2230/205* (2013.01); *A61M 2230/40* (2013.01)

(58) Field of Classification Search
CPC .............. A61M 16/00; A61M 16/0003; A61M 16/0015; A61M 16/0027; A61M 16/0051; A61M 2230/40; A61M 16/0069
See application file for complete search history.

(56) References Cited

U.S. PATENT DOCUMENTS

| | | | |
|---|---|---|---|
| 6,401,713 B1 * | 6/2002 | Hill ....................... | A61M 16/00 128/204.18 |
| 6,550,478 B2 | 4/2003 | Remmers et al. | |
| 7,469,698 B1 * | 12/2008 | Childers ............... | A61M 16/00 128/204.18 |
| 8,365,729 B2 | 2/2013 | Alder et al. | |

(Continued)

FOREIGN PATENT DOCUMENTS

WO     WO2010097718 A1     9/2010

OTHER PUBLICATIONS

International Search Report and Written Opinion for PCT/US2014/068214. Issued on Feb. 23, 2015.

*Primary Examiner* — Valerie L Woodward
(74) *Attorney, Agent, or Firm* — Stetina Brunda Garred and Brucker; Mark Garred

(57) ABSTRACT

Adapting a patient to an airway pressure support therapy is disclosed. An initial prescription pressure level is derived from a respiratory disturbance index diagnosis. A pressure ramping slope is generated from the initial prescription pressure level and a received initial pressure level. Increasing levels of pressure are delivered to the patient as defined by the pressure ramping slope. The pressure ramping slope is adjusted based upon derived usage duration trends, and the prescription pressure level is adjusted based upon measured apnea/hypopnea index variations resulting from the delivered increasing levels of pressure to the patient.

19 Claims, 4 Drawing Sheets

(56) References Cited

U.S. PATENT DOCUMENTS

| | | |
|---|---|---|
| 2003/0055346 A1 | 3/2003 | Rapoport et al. |
| 2004/0016433 A1* | 1/2004 | Estes ............... A61M 16/00 128/204.21 |
| 2004/0244807 A1 | 12/2004 | Sun et al. |
| 2008/0053440 A1* | 3/2008 | Farrugia ............ A61M 16/00 128/204.23 |
| 2008/0060647 A1* | 3/2008 | Messenger ......... A61M 16/00 128/204.23 |
| 2009/0038616 A1* | 2/2009 | Mulcahy ......... A61M 16/0051 128/204.23 |
| 2009/0139523 A1 | 6/2009 | Ayappa et al. |
| 2011/0061647 A1 | 3/2011 | Stahmann et al. |

\* cited by examiner

CONTINUOUS POSITIVE AIRWAY PRESSURE THERAPY AUTO-TITRATION

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates generally to the treatment of respiratory conditions with continuous positive airway pressure (CPAP) devices, and more particularly, to auto-titration of prescription pressure to improve comfort for patients beginning CPAP therapy.

2. Related Art

Sleep apnea is a serious medical condition in which patient breathing during sleep pauses abnormally, or is abnormally low. Apnea is categorized as obstructive, central, and combined obstructive and central, though the obstructive sleep apnea (OSA) is the most common. The patient's upper airway repeatedly narrows or collapses, causing pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles resulting from patients gasping for air. There have been studies linking sleep apnea to more severe long-term health issues including heart disease and depression, and recently, to cancer as well. With apnea being strongly linked to obesity, and with obesity being projected to increase, the number of patients suffering from sleep apnea is likely to increase concomitantly.

One common treatment for obstructive sleep apnea is continuous positive airway pressure (CPAP) therapy, where a positive pressure is applied to the patient to prevent its collapse as would otherwise occur during an apnea episode. By retaining the patient's airway, normal, uninterrupted breathing during sleep is ensured. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. Earlier patient breathing assistance devices tended to be uncomfortable to use because of the bulkiness associated with the patient interface, as well as the misapplication of pressure resulting from sub-optimal control methodologies. Various improvements have been developed to reduce discomfort during therapy, particularly at critical points along the patient's respiratory cycle. Thus, what was previously prescribed only for the more severe cases of sleep apnea in which the benefits of treatment outweighed the significant discomfort is now useful for treating a wider spectrum of sleep apnea conditions.

Although a properly set therapeutic pressure level alleviates apnea and hypopnea conditions, a determination of the required pressure balanced against the comfort demands of the patient may involve complicated diagnostics and/or several sleep cycles of trial-and-error adjustments. As a general matter, the application of pressure against the respiratory efforts of the patient and consequent increase in work of breathing may induce a sense of asphyxiation, so any excess therapeutic pressure causes needless discomfort.

Conventionally, most patients begin CPAP treatment following a diagnostic test at a sleep lab. Such sleep studies are understood to involve the measurement of several sleep indicators including an apnea and hypopnea index (AHI). When the AHI exceeds a threshold value more than five times an hour, that patient is deemed to be suffering from obstructive sleep apnea and hence in need of treatment. The following night, the patient is scheduled for titration, which also takes place in the sleep lab, and involves attempting the reduction of the AHI to less than five events per hour by increasing pressure. Pressure increases are typically applied when the patient is in a sleep state, and thereby avoiding the aforementioned feeling of asphyxiation that may otherwise occur as a result of pressure against breathing efforts in a wakeful state.

After titration, the patient is prescribed a CPAP device for home use. During initial treatment, because of the unfamiliar sensations that the patient may experience as a result of the applied airway pressure, there may be significant discomfort. This discomfort may be so severe that the patient detrimentally stops treatment. In response, the medical practitioner may prescribe a bi-level device that improves comfort and reduces the feelings of asphyxiation, particularly during the wakeful states. Bi-level devices are understood to apply two different pressure levels depending on the respiratory phase—higher pressures during inspiration, and lower pressures during exhalation. Thus, in summary, a typical patient suffering from sleep apnea/hypopnea first undergoes a diagnostic step, followed by a titration step in the sleep lab, followed by a trial step of using the CPAP device and experiencing discomfort, and a treatment modification step to change to a bi-level device to assist with compliance.

Alternatively, the sleep study may be omitted and instead substituted with a home-use diagnostic device in the interest of cost reduction in the diagnosis and treatment of sleep apnea/hypopnea. The diagnostic device is used on a single night, and returned to a laboratory where the results are analyzed. The turnaround for this service may be a few days, and if apnea/hypopnea is detected in the patient, e.g., the calculated AHI is greater than 5 per hour, the patient may be provided with an automatically titrating CPAP device. The typical protocol is to start pressure at low levels, for example, 4 cm $H_2O$, and in response to the patient experiencing apneic events, gradually increasing pressure on an event-by-event basis to reach a therapeutic pressure.

There are several disadvantages associated with such automatic titration, also referred to in the art as auto-CPAP. One issue is that the patient is under-titrated on any given night because the increase in pressure is in response to an apnea event. Thus, there is discomfort and sleeplessness associated with being aroused awake because of the apnea/hypopnea condition, possibly over an extended duration. In other words, the therapeutic effects of using the CPAP device may be minimal. Another issue is that the titration is set most suitably for apneas and hypopneas, and does not account for the discomfort associated with ariophagia (air entering the stomach) or over-titration that may not account for central apnea. Conventional titration techniques tend to disregard patient comfort and instead operate under the expectation that the patient will eventually become accustomed. However, this expectation tends to have the opposite effect of discouraging treatment compliance.

Accordingly, there is a need in the art for improved CPAP automatic titration that transitions the patient from a minimized, comfortable level to full prescription level while maintaining comfortable pressure levels at any given point in treatment, including the initial phases when the patient is becoming accustomed to the resistance against constant pressure. There is also a need in the art for minimizing AHI despite the presence of untreatable central apnea without over-titration.

BRIEF SUMMARY

The present disclosure contemplates improvements to obstructive sleep apnea treatments in which patients are diagnosed, titrated to adaptation and comfort, and then further titrated to reduce the patient's apnea/hypopnea index (AHI). Various embodiments are directed to tuning the delivery of patient airway pressure to allow the patient to easily adapt to CPAP therapy, and based upon certain metrics of that patient's adaptation to increasing levels of pressure, adjusting the titration to the prescribed pressure level to achieve a full reduction of AHI. Additionally envisioned is the determination of the minimum AHI that can be achieved in the presence of central apnea, which cannot be treated by CPAP therapy alone.

In accordance with one embodiment, there is a method for adapting a patient to an airway pressure support therapy. The method may include deriving an initial prescription pressure level from a respiratory disturbance index diagnosis. Thereafter, the method may include generating a pressure ramping slope from the initial prescription pressure level and a received initial pressure level. There may also be a step of delivering increasing levels of pressure to the patient as defined by the pressure ramping slope. The method may include adjusting the pressure ramping slope based upon derived usage duration trends, and adjusting the prescription pressure level based upon measured apnea/hypopnea index variations resulting from the delivered increasing levels of pressure to the patient.

According to another embodiment of the disclosure, a method for titrating a patient to prescription airway pressure with a continuous positive airway pressure (CPAP) therapy device is contemplated. The method may include generating an initial respiratory disturbance index based upon patient oxygen saturation measurements, patient interface pressure measurements, and machine pressure measurements during a diagnostic mode. Additionally, there may be a step of setting a diagnosed treatment pressure level and a starting pressure level. The method may also include generating an initial pressure ramping strategy from the diagnosed treatment pressure level, the starting pressure level, and a default ramp duration. Thereafter, there may be a step of applying the initial pressure ramping strategy to the patient during a titration mode. The method may include deriving a usage trend from a median use duration and a weighted average of use durations over one or more sessions for a predetermined duration window. Furthermore, there may be a step of generating a secondary pressure ramping strategy from the initial treatment pressure level, and the default ramp duration adjusted in response to the usage trend. The method may also include applying the secondary pressure ramping strategy to the patient during a subsequent session in the titration mode.

Certain other embodiments of the present disclosure contemplate a non-transitory program storage medium readable by a data processor of a CPAP therapy device that tangibly embodies one or more programs of instructions executable by the data processor to perform the foregoing method. The present disclosure will be best understood accompanying by reference to the following detailed description when read in conjunction with the drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

The detailed description set forth below in connection with the appended drawings is intended as a description of certain embodiments of the presently disclosed auto-titration for continuous positive airway pressure therapy. Generally, treatment begins with diagnosis, followed by titration to adaptation and comfort e.g., ramping up pressure in accordance with the patient's comfort level, and then evolving titration to reduce the patient's apnea/hypopnea index.

The description sets forth the various functions in connection with the illustrated embodiments, but it is to be understood, however, that the same or equivalent functions may be accomplished by different embodiments that are also intended to be encompassed within the scope of the present disclosure. As such, the particular disclosures herein are not intended to represent the only forms that may be developed or utilized. It is further understood that the use of relational terms such as first and second and the like are used solely to distinguish one entity from another without necessarily requiring or implying any actual such relationship or order between such entities.

Figure 1:
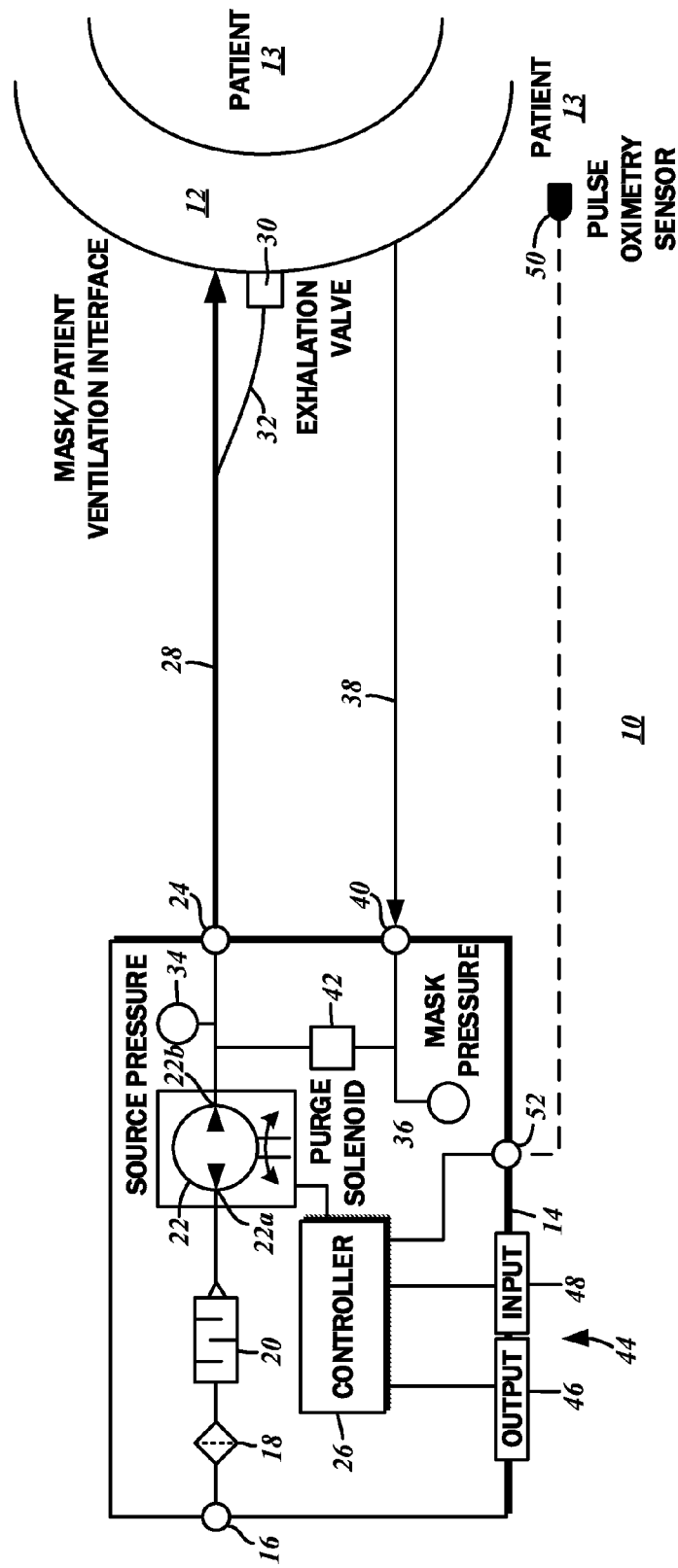
FIG. 1 is a block diagram showing the various components of a CPAP apparatus in accordance with various embodiments of the present disclosure including a typical ventilation unit, a patient ventilation mask, gas passage conduits, and a pulse oximetry sensor.

The block diagram of FIG. 1 illustrates an exemplary airway support device 10 in which various embodiments of the present disclosure may be implemented. There is a mask or patient ventilation interface 12, and a ventilation unit 14. The following disclosure will make reference to the patient ventilation interface 12 and the mask interchangeably. It is understood to be an apparatus such as a full-face mask or a nasal pillows mask that can be placed in direct gas flow communication with the upper respiratory tract, i.e., the nasal cavity and/or the oral cavity, of a patient 13. It will be appreciated that other apparatuses that so interface the respiratory tract of the patient 13 to the ventilation unit 14 may be substituted without departing from the scope of the present disclosure.

The ventilation unit 14 generates a flow of breathing gas that is delivered to the patient via the patient ventilation interface 12. The breathing gas may be ambient air, a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a ventilation source 22, which may be a centrifugal fan, blower, or any other suitable device that generates gas flow and pressure suitable for splinting a patient's airway with Continuous Positive Airway Pressure (CPAP) in accordance with the present disclosure. The ventilation source 22 has an inlet port 22a coupled to the sound suppressor 20, and an outlet port 22b that is in gas flow communication with an outlet port 24 of the ventilation unit 14.

The ventilation source 22 is driven electrically and its actuation is governed by a controller 26, which implements various methods of CPAP treatment such as those disclosed in the co-pending U.S. patent application Ser. No. 13/411,257 entitled "DUAL PRESSURE SENSOR CONTINUOUS POSITIVE AIRWAY PRESSURE (CPAP) THERAPY," filed Mar. 2, 2012, the disclosure of which is hereby incorporated by reference in its entirety herein. Along these lines, the controller 26 is understood to include a data processing device that receives predetermined instructions to perform various operations, and generate outputs in response. Thus, the contemplated methods for titrating the patient 13 to prescription airway pressure can be at least partially implemented therewith.

The flow of breathing gas that is output from the ventilation source 22 is passed through the outlet port 24 to a gas conduit 28 that is coupled to the aforementioned patient ventilation interface 12. The gas conduit 28 is understood to be a plastic tube having a predetermined inner diameter such as 22 mm or smaller, though any other conduit of suitable material and construction may be utilized. The patient ventilation interface 12 in accordance with various embodiments of the present disclosure also includes a piloted valve 30 that is selectively actuated depending on the pressure differential between the patient ventilation interface 12 and the ventilation unit 14. The piloted valve 30 is connected to a pilot line 32 that branches from the gas conduit 28. A pressure difference is generated between the patient ventilation interface and the exhalation valve, such that it is closed during inspiration and opened during expiration. It will be appreciated that the specifics of the patient ventilation interface 12, including the piloted valve 30 thereof, are presented by way of example only and not of limitation. Any other suitable patient ventilation interface 12, including those that may be utilized in conjunction with different variations of the ventilation unit 14, may be substituted without departing from the scope of the present disclosure.

In order to ascertain such pressure differentials, the presently contemplated airway support device 10 includes dual pressure sensors, including a source pressure sensor 34 and a patient interface pressure sensor 36. The source pressure sensor 34 is disposed within the ventilation unit 14, and monitors the pressure at the outlet port 22b. The patient interface pressure sensor 36 is also physically disposed within the ventilation unit 14, but is in direct gas flow communication with the patient ventilation interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 39. This can be done through a purge solenoid 42 connected to both. The purge can be continuous or intermittent according to the patient's breathing phase or pressure difference between the blower pressure and the mask pressure.

Along the lines of the source pressure sensor 34 and the patient interface pressure sensor 36, the embodiments of the present disclosure further contemplate additional patient readings. More particularly, there is a pulse oximetry sensor 50 that can be attached to the patient 13 to measure blood oxygen saturation. As shown in the block diagram of FIG. 1, the pulse oxyimetry sensor 50 may communicate with the ventilation unit 14 through an input port 52 to feed the measured data to the controller 26 for further processing and response. It will be recognized by those having ordinary skill in the art that there are numerous variations of the pulse oximetry sensor 50. Although illustrated as being attached to the finger of the patient 13, the pulse oximetry sensor may be attached to any suitable appendage. Furthermore, the connection to the ventilation unit 14 may be wired or wireless, and the embodiment shown in FIG. 1 is by way of example only and not of limitation. Thus, the input port 52 may be a wired interface, or a wireless interface.

As indicated above, the sequence and timing of delivering gas flow to the patient 13 are governed by the specific treatment modalities that utilize feedback data from the pressure sensors 34, 36. The setting of options relating to the treatment modalities, along with the starting and stopping of treatment is possible via a user interface 44 coupled to the controller 26, which includes an output or display interface 46, as well as an input interface 48. Various embodiments of the present disclosure contemplate methods for tuning the pressures delivered to the patient 13 on a daily basis to allow easy adaptation. After knowing how the patient 13 adapts successfully to the gradual increases in pressure, the patient 13 is titrated to the necessary prescription pressure level that will achieve a full or at least partial reduction in the apnea/hypopnea index.

Figure 2:
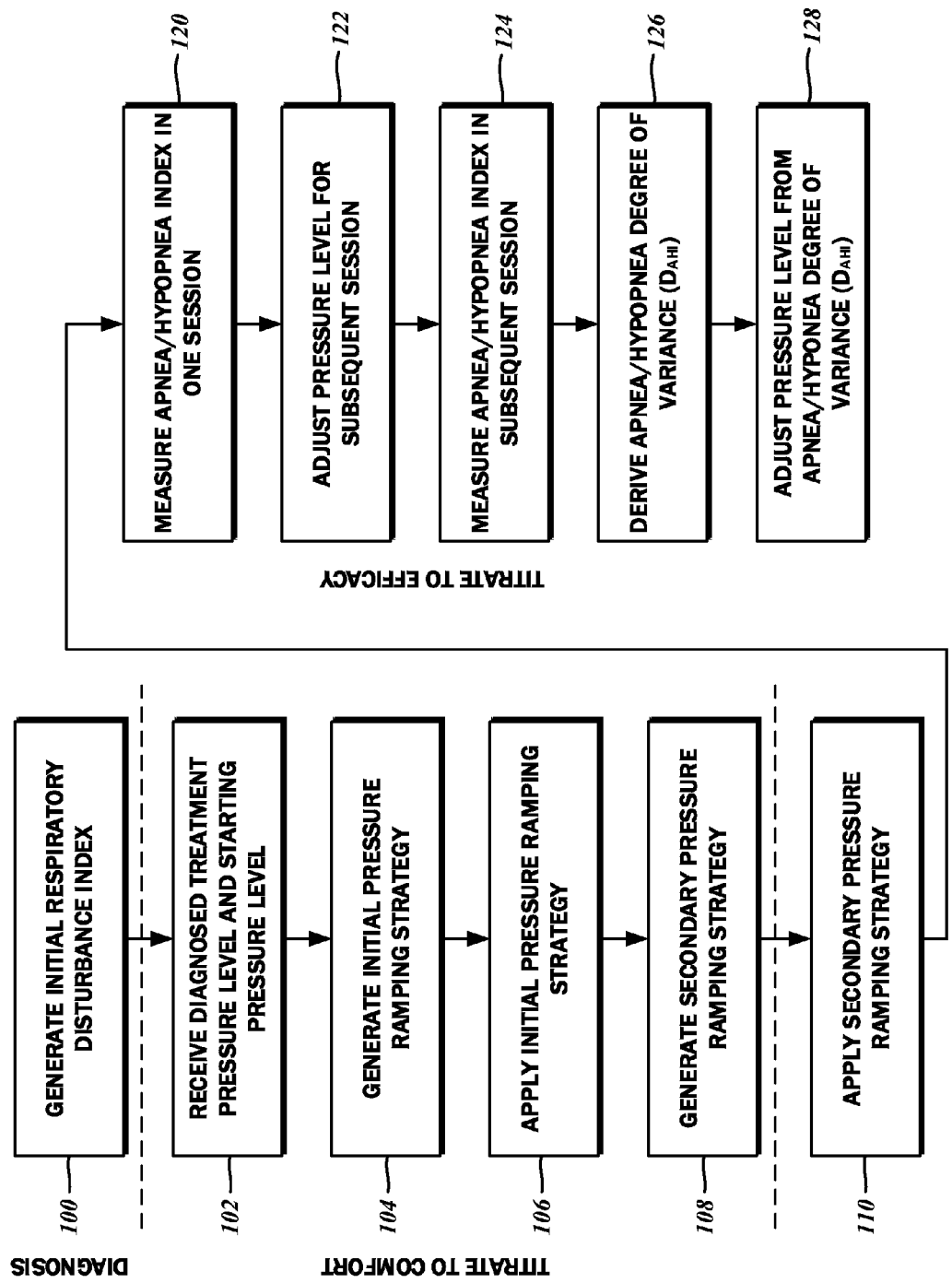
FIG. 2 is a flowchart depicting one embodiment of a method for titrating a patient to a comfortable prescription airway pressure while reducing occurrences of sleep apnea/hypopnea.

With reference to the flowchart of FIG. 2, one embodiment of the presently disclosed method for titrating the patient 13 to prescription airway pressure with the CPAP/airway support device 10 includes a step 100 of generating an initial respiratory disturbance index (RDI). This step is undertaken during a diagnostic mode, which typically continues throughout the first night that the patient 13 is using the airway support device 10 with no pressure being delivered, and with the pulse oximetry sensor 50 being coupled to the patient 13.

Again, it is understood that the pulse oximetry sensor 50 measures the patient's $O_2$ saturation, and provides the measurement data to the ventilation unit 14 via the input port 52. More particularly, the measurement data, which is reported as a saturation percentage, is fed to the controller 26 where it is processed further in accordance with the following method.

The respiratory disturbance index (RDI) is contemplated to be a tally of the number of instances within a time range that an event or condition that is known or tends to correspond to a disturbance in the patient's respiration. These instances may be detected with the aforementioned pulse oximetry sensor 50, as well as a combination of the source pressure sensor 34 and the patient interface pressure sensor 36. For example, when the pulse oximetry sensor 50 detects a $O_2$ saturation that is less than a predetermined threshold percentage, the RDI can be incremented. As another example, the RDI may be incremented when a patient flow estimate drops below a predetermined threshold rate. As is understood, the patient flow rate may be derived from a combination of measurements from the source pressure sensor 34 and the patient interface pressure sensor 36. The presence or absence of obstructive sleep apnea or hypopnea can be detected based upon the RDI.

Once the presence of apnea/hypopnea has been established during an entire night of diagnosis the method may continue with a step 102 of setting a diagnosed treatment pressure level, also referenced as $CPAP_{Rx0}$, and a starting pressure level, also referenced as $CPAP_0$. As utilized herein, setting as pertaining to the treatment pressure level may refer to the transfer of a numerical value thereof calculated from the RDI. This calculation, by way of example only, may be the sum of a first constant value and an integer division result of the RDI and a second constant value, minus 20% of the difference between the mean saturated oxygen percentage ($M_{Sat\%}$) during the diagnostic mode and a third constant value. The result may be given in terms of pressure, e.g., cm $H_2O$. The calculation may also be described thus: $CPAP_{Rx0}=8+(RDI/30)-0.2\,(M_{Sat\%}-90)$ [cm $H_2O$]. The first constant is 8, the second constant is 30, and the third constant is 90. More generally, $CPAP_{Rx}O=f_1(RDI, M_{Sat\%})$, that is, the diagnosed treatment pressure level is generated from a function of the initial RDI and a mean of the patient oxygen saturation measurements. For example, if RDI was determined to be 34, then the integer division operation would result in 1. Continuing the example, if $M_{Sat\%}$ was determined to be 95%, the second operand in the subtraction would be 0.2(95−90), or 0.2(5), or 1.0. Thus, $CPAP_{Rx0}$ would be set to 9 cm $H_2O$-1.0, or 8 cm $H_2O$.

Although the diagnosis-based calculation of the treatment pressure level is contemplated in accordance with various embodiments of the present disclosure, it is also possible to independently conduct a sleep study to determine this value, and input the same to the ventilation unit 14 via the user interface 44. Along these lines, the starting pressure level depends upon a subjective patient comfort, and may be manually set at a predetermined value via the same user interface 44. One possible default value of the starting pressure level is 4 cm $H_2O$, though this is by way of example only and not of limitation.

Figure 3:
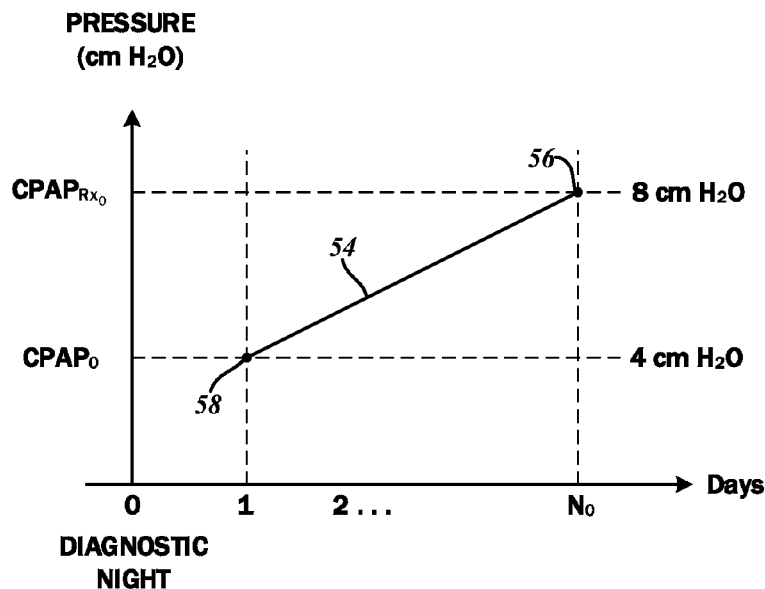
FIG. 3 is a graph illustrating an initial pressure ramping slope or initial pressure ramping strategy.

With additional reference to the graph of FIG. 3, the method continues with a step 104 of generating an initial pressure ramping strategy, which in the illustrated example, is a pressure ramping slope 54. This is generated from the diagnosed treatment pressure level or $CPAP_{Rx0}$ 56, the starting pressure level $CPAP_0$ 58, and a default ramp duration. Proceeding along with the previous example, $CPAP_{Rx0}$ is set to 8 cm $H_2O$, while $CPAP_0$ is set to 4 cm $H_2O$. The default ramping duration is given as an indeterminate value $N_0$, given in terms of days. Although the present disclosure contemplates adjustments made over one or more days, any other frame of reference to distinguish one treatment instance or session from another may be substituted.

The method continues with a step 106 of applying the initial pressure ramping strategy during a titration mode as calculated above. Generally, this contemplates delivering increasing levels of pressure to the patient as defined by the pressure ramping slope 54. In the first night in the titration mode, shown as day 1 of the graph of FIG. 3, the patient 13 is delivered the starting pressure level $CPAP_0$.

Prior to beginning treatment in the second day but after completion of the first day, there is sufficient information to determine whether the ramping duration $N_0$ needs to be extended or shortened depending on patient comfort levels. The method thus further includes a step 108 of deriving a usage trend from a median use duration and a weighted average of use durations over one or more sessions for a predetermined window. In the most basic iteration where there is one use duration historical data, this predetermined window is one day. The use relates to the number of hours in the day that the patient 13 is undergoing therapy with the airway support device 10.

Both the median and the weighted average are calculated over a window of N days. For the first day, the median is given as ($H_m(1)$), while the weighted average is given as $H_w(1)$. The median is understood to provide a long term perspective of the hours of use, and the weighted average is understood to represent the latest trend. An increasing use trend may mean that the patient 13 is becoming accustomed to the therapy, while decreasing use may mean that the patient 13 is becoming more uncomfortable with the higher pressure levels. A steady or constant use may mean that the patient 13 has settled into a comfort zone. Thus, various embodiments of the method contemplate responsive actions to these trends, including extending or shortening the ramp duration, which has the effecting of decreasing or increasing the pressure ramping slope 54, respectively.

The exact number of days to offset is given by ΔN, which for the window encompassing only day 1 is ΔN(1), and is based upon a function $f_2$ of the median $H_m$, and the weighted average $H_w$. That is, $f_2=(H_w(1), H_m(1))$. Referring to the graph of FIG. 3, where in each of the quadrants that the values for $H_w$ and $H_m$ fall determines the action taken on ΔN. A first quadrant 60a is defined by a lower threshold median of 2, and an upper threshold weighted average of 2. There is no upper threshold median. For such values of $H_w$ and $H_m$, ΔN is contemplated to be zero (0). A second quadrant 60b is defined by a lower threshold median of 2, and a lower threshold weighted average of 2, and there is no upper threshold weighted average. In this case, ΔN involves a reduction of 1 day. A third quadrant 60c is defined by an upper threshold median of 0 as well as an upper threshold weighted average of 2. In such case, ΔN is increased by one day. A fourth quadrant 60d is defined by an upper threshold median of 2 and a lower threshold weighted average of 2, with no upper threshold weighted average. Here, ΔN is decreased by one day. It will be appreciated by those having ordinary skill in the art that the threshold median values and threshold weighted average of 2 is presented by way of example only and not of limitation. Any other suitable threshold may be substituted without departing from the scope of the present disclosure.

Figure 4:
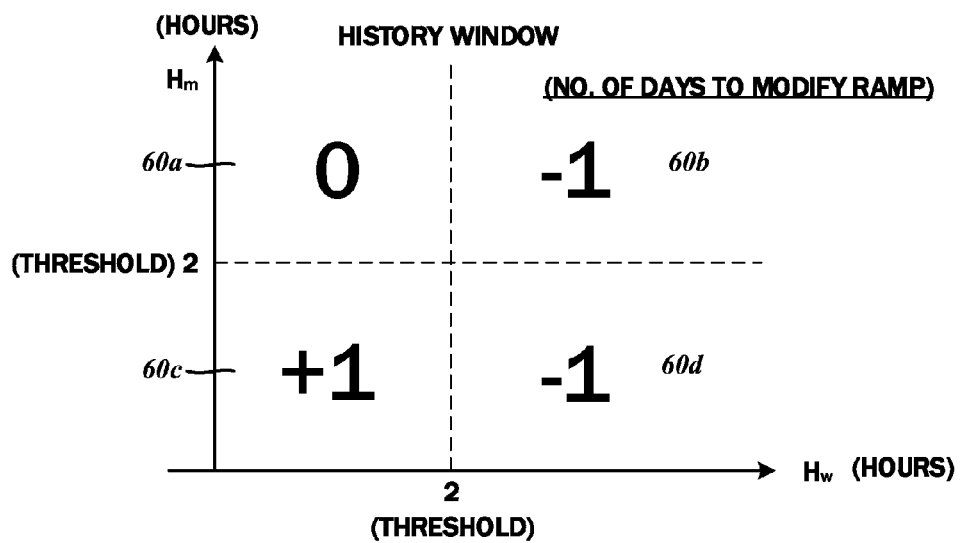
FIG. 4 is a graph showing different regions of possible values that a usage duration trend may have and its corresponding pressure ramping slope adjustments.

In order for the ramp duration to be decreased by one day, the intersection of the values of the weighted average $H_w$ and the median $H_m$ falls into the second or fourth quadrants 60b, 60c shown in FIG. 4. For example, $H_w(1)$ may be three (3) hours, and $H_m(1)$ may also be three (3) hours; in which case, being that the intersection of $H_w(1)$ and $H_m(1)$ falls into the second quadrant 60bb, $\Delta N$ is −1. Therefore, $N_1=N_0-1$, or −1 day.

Figure 5:
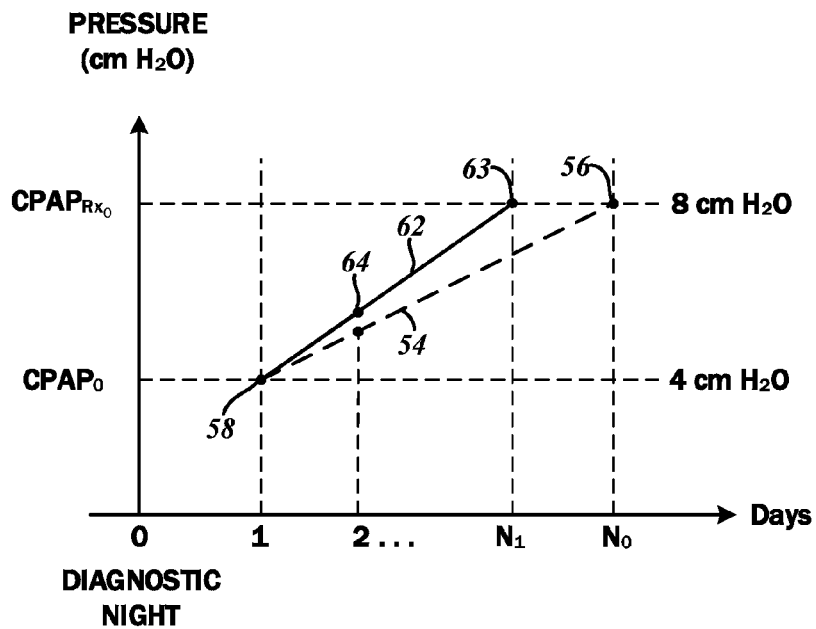
FIG. 5 is a graph of the initial pressure ramping slope and an adjusted pressure ramping slope after the ramping duration has been shortened.

As shown in the graph of FIG. 5, shortening the ramp duration by one day adjusts the final ending day to reach $CPAP_{Rx0}$ to occur one day earlier at point 63. The prescription pressure level $CPAP_{Rx0}$ is not understood to change in response to the foregoing usage trends. The method accordingly includes a step 108 of generating a secondary pressure ramping strategy. $N_1$ is understood to generally refer to the change (whether increasing, decreasing, or constant duration) to the original duration $N_0$, that is $N_1=N_0+\Delta N(1)$. This alternative ramping strategy is generated from the initial treatment pressure level 58, and a steeper, alternative pressure ramping slope 62 that has been adjusted from the previous pressure ramping slope 54. Given the appropriate conditions of $H_w$ and $H_m$, it is also contemplated that no changes to the ramping duration are made at all.

Assuming the pressure level for the current day is being generated prior to beginning treatment, the new ramping slope 62 coincides with the current date at a ramp pressure level 64. Along these lines, there is a step 110 of applying the secondary pressure ramping strategy to the patient during a subsequent session in the treatment ramping mode. It is therefore contemplated that the pressure ramping slope, as well as the pressure applied on any given day, is adjusted based upon derived usage duration trends.

Extending the foregoing examples and principles to a given day k, the change in ramping duration on such day is given by $\Delta N(k)=f_2(H_w(k), H_m(k))$. Again, $H_w(k)$ is understood to be the weighted average of use hours per day, and $H_m(k)$ is understood to be the median hours use on a given window of N days. As such, the number of days to extend or shorten the ramp by, at day k, is given as $N_k=N_{k-1}+\Delta N(k)$. If $N_k$ is not equal to $N_{k-1}$, then a new pressure value is calculated for that day based on the new ramp slope. In further detail, the slope $M_k$ is given by the diagnosed treatment pressure level $CPAP_{Rx0}$ over the number of days to which the ramp has been adjusted, $N_k$, or $CPAP_{Rx0}/N_k$. Thus, $CPAP_{k+1}$, the pressure level on the day of concern, is: $M_{k-1}*(k-1)+CPAP_0$.

The foregoing procedure of modifying the ramp adjusts for patient comfort. The presently disclosed methods also contemplate further titration to minimize the patient's apnea/hypopnea index (AHI) while maintaining comfort. As indicated above, it is possible to determine the minimum AHI that can be achieved despite the presence of central apneas that cannot be treated with CPAP. This involves, generally, adjusting delivered pressure to the measured AHI whenever pressure is increased on the day/session before. The change in AHI ($\Delta AHI$) that is in reaction to a given change in CPAP pressure ($\Delta CPAP$) is defined as $D_{AHI}$.

Accordingly, per step 120, the method may also include measuring an apnea/hypopnea index during one session/day in the titration mode, followed by a step 122 of adjusting the diagnosed treatment pressure level for another, subsequent session/day based upon the measured AHI. Furthermore, there is a step 124 of measuring the AHI during the subsequent session/day, then a step 126 of deriving an AHI degree of variance, e.g., $D_{AHI}$.

The AHI degree of variance is derived from a difference between the measured AHI in the one session and the measured AHI in the subsequent session, that is, $\Delta AHI$. Additionally, the adjustment to the diagnoses treatment pressure level, e.g. $\Delta CPAP$, is part of the derivation step of the $D_{AHI}$. More particularly, $\Delta CPAP$ is understood to be the predefined pressure increase between the previous day/session and the day/session before. The prescription pressure level for the subsequent day/session, $CPAP_{Rxk}$, is $CPAP_{Rxk-1}+f_4(D_{AHI}^{k-1}, AHI^{k-1})$.

Figure 6:
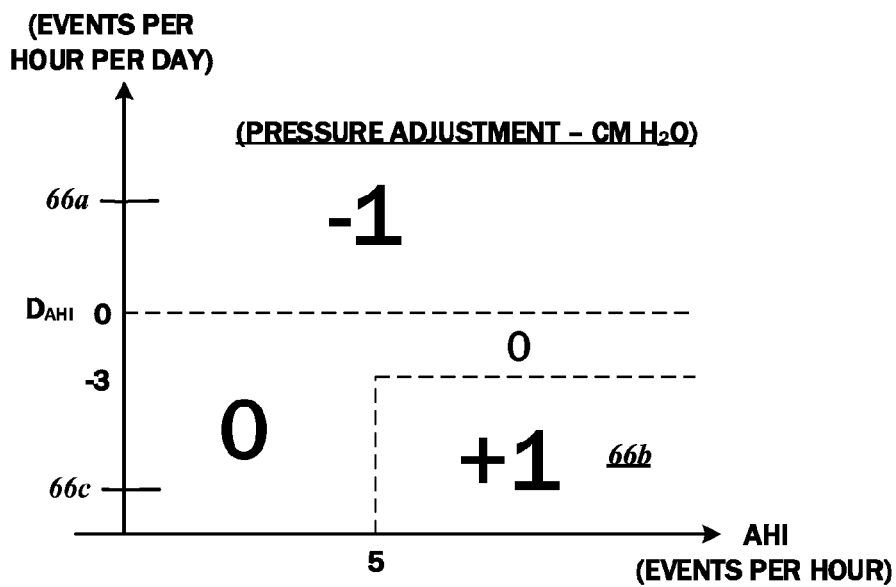
FIG. 6 is a graph showing different regions of possible values that apnea/hypopnea index variations may have and its corresponding prescription pressure level adjustments.

The function is the estimated change $D_{AHI}^{k-1}$ on day k−1, and AHI is understood to be the apnea/hypopnea index on day k−1. Referring to the plot of FIG. 6, the outcomes of function $f_4$ for given values of $D_{AHI}$ and AHI are shown. There are three general regions: a first region with a minimum $D_{AHI}$ of 0 (but no maximum), which represents the condition where the last increase in pressure worsened the titration efforts; a second region 66b with a minimum AHI of 5, and a maximum $D_{AHI}$ of −3; and a third region 66c defined by a combined area with a maximum AHI of 5 and a $D_{AHI}$ of less than zero, and a minimum $D_{AHI}$ of −3 but with an unlimited AHI, which represents the AHI of patients suffering from central apnea and other conditions untreatable with CPAP alone.

Following the derivation of $D_{AHI}$, the method continues with a step 128 of adjusting the diagnosed treatment pressure level based on such derived apnea/hypopnea index degree of variance. When the combination of the AHI and $D_{AHI}$ are within the first region 66a, then the treatment pressure level is decreased by 1 cm $H_2O$. When the combination of the AHI and $D_{AHI}$ are within the second region 66b, the treatment pressure level is increased by 1 cm $H_2O$. If the combination of AHI and $D_{AHI}$ are such that they fall within the third region 66c, is understood that the titration goal has been reached and no further changes to the delivered pressure are necessary. The foregoing steps can be summarized as adjusting the prescription pressure level based upon measures apnea/hypopnea variations resulting from the delivered increasing levels of pressure to the patient.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present disclosure with more particularity than is necessary, the description taken with the drawings making apparent to those skilled in the art how the several forms of the present disclosure may be embodied in practice.

What is claimed is:

1. A method for adapting a patient to an airway pressure support therapy, the method comprising:
   deriving an initial prescription pressure level from a respiratory disturbance index diagnosis;
   generating a pressure ramping slope from the initial prescription pressure level and a received initial pressure level;
   delivering increasing levels of pressure to the patient as defined by the pressure ramping slope;
   adjusting the pressure ramping slope based upon derived usage duration trends; and
   adjusting the prescription pressure level based upon measured apnea/hypopnea index variations resulting from the delivered increasing levels of pressure to the patient;
   wherein the usage duration trends are derived from a median use duration and a weighted average of use durations over one or more sessions for a predetermined duration window.

2. The method of claim 1, wherein the apnea/hypopnea index variations is based upon a measurement of the apnea/hypopnea index during one session, a subsequent measurement of the apnea/hypopnea index during another session.

3. The method of claim 2, wherein the secondary pressure ramping strategy includes an adjustment to the default ramp duration.

4. The method of claim 3, wherein the default ramp duration is increased in response to a decreasing usage trend.

5. The method of claim 3, wherein the default ramp duration is decreased in response to an increasing usage trend.

6. The method of claim 2, wherein the initial respiratory disturbance index is incremented at every occurrence of the oxygen saturation measurement dropping below a predetermined threshold value during the diagnostic mode.

7. The method of claim 2, wherein the starting pressure level is manually entered into a user interface of the CPAP therapy device.

8. The method of claim 2, wherein the initial respiratory disturbance index is incremented at every occurrence of a patient flow estimate derived from the patient interface pressure measurements and the machine pressure measurements dropping below a predetermined threshold value during the diagnostic mode.

9. The method of claim 8, wherein the diagnosed treatment pressure level is generated from a function of the initial respiratory disturbance index and a mean of the patient oxygen saturation measurements made during the diagnostic mode.

10. The method of claim 8, further comprising:
measuring an apnea/hypopnea index during one session in the titration mode; and
adjusting the diagnosed treatment pressure level for another subsequent session based upon the measured apnea/hypopnea index in the one session.

11. The method of claim 10, further comprising:
measuring the apnea/hypopnea index during the subsequent session;
deriving an apnea/hypopnea index degree of variance from a difference between the measured apnea/hypopnea index in the one session and the measured apnea/hypopnea index in the subsequent session and the adjustment to the diagnosed treatment pressure level; and
adjusting the diagnosed treatment pressure level based upon the derived apnea/hypopnea index degree of variance.

12. The method of claim 11, wherein the diagnosed treatment pressure level is decreased when there is a positive apnea/hypopnea index degree of difference.

13. The method of claim 11, wherein the diagnosed treatment pressure is increased when there is a negative apnea/hypopnea index degree of difference over a first predetermined limit and the measured apnea/hypopnea index in the one session is greater than a second predetermined limit.

14. The method of claim 11, wherein the diagnosed treatment pressure is unmodified when there is a negative apnea/hypopnea index degree of difference less than a first predetermined limit and the measured apnea/hypopnea index in the one session is greater than a second predetermined limit.

15. The method of claim 11, wherein the diagnosed treatment pressure is unmodified when there is a negative apnea/hypopnea index degree of difference less than a first predetermined limit and the measured apnea/hypopnea index in the one session is less than a second predetermined limit.

16. A method for titrating a patient to prescription airway pressure with a continuous positive airway pressure (CPAP) therapy device, the method comprising:
generating an initial respiratory disturbance index based upon patient oxygen saturation measurements, patient interface pressure measurements, and machine pressure measurements during a diagnostic mode;
setting a diagnosed treatment pressure level and a starting pressure level;
generating an initial pressure ramping strategy from the diagnosed treatment pressure level, the starting pressure level, and a default ramp duration;
applying the initial pressure ramping strategy to the patient during a titration mode;
deriving a usage trend from a median use duration and a weighted average of use durations over one or more sessions for a predetermined duration window;
generating a secondary pressure ramping strategy from the initial treatment pressure level, and the default ramp duration adjusted in response to the usage trend; and
applying the secondary pressure ramping strategy to the patient during a subsequent session in the titration mode.

17. An article of manufacture comprising a non-transitory program storage medium readable by a data processor of a CPAP therapy device, the medium tangibly embodying one or more programs of instructions executable by the data processor to perform a method for titrating a patient to prescription airway pressure with the CPAP therapy device, the method comprising:
generating an initial respiratory disturbance index based upon patient oxygen saturation measurements, patient interface pressure measurements, and machine pressure measurements during a diagnostic mode;
setting a diagnosed treatment pressure level and a starting pressure level;
generating an initial pressure ramping strategy from the diagnosed treatment pressure level, the starting pressure level, and a default ramp duration;
applying the initial pressure ramping strategy to the patient during a titration mode;
deriving a usage trend from a use duration for a single session and a weighted average of use duration over one or more sessions for a predetermined duration window;
generating a secondary pressure ramping strategy from the initial treatment pressure level, and the default ramp duration adjusted in response to the usage trend; and
applying the secondary pressure ramping strategy to the patient during a subsequent session in the titration mode.

18. The article of manufacture of claim 17, wherein the secondary pressure ramping strategy includes an adjustment to the default ramp duration.

19. The article of manufacture of claim 17, wherein the method further includes the steps of:
measuring an apnea/hypopnea index during one session in the titration mode; and
adjusting the diagnosed treatment pressure level for another subsequent session based upon the measured apnea/hypopnea index in the one session;
measuring the apnea/hypopnea index during the subsequent session;
deriving an apnea/hypopnea index degree of variance from a difference between the measured apnea/hypopnea index in the one session and the measured apnea/ hypopnea index in the subsequent session and the adjustment to the diagnosed treatment pressure level; and adjusting the diagnosed treatment pressure level based upon the derived apnea/hypopnea index degree of variance.

* * * * *